United States Patent
Hyun

(10) Patent No.: US 9,974,483 B2
(45) Date of Patent: May 22, 2018

(54) NON-INVASIVE BLOOD MEASURING DEVICE

(71) Applicant: Ki Bong Hyun, Seoul (KR)

(72) Inventor: Ki Bong Hyun, Seoul (KR)

( * ) Notice: Subject to any disclaimer, the term of this patent is extended or adjusted under 35 U.S.C. 154(b) by 117 days.

(21) Appl. No.: 15/119,773

(22) PCT Filed: Dec. 9, 2014

(86) PCT No.: PCT/KR2014/012066
§ 371 (c)(1),
(2) Date: Aug. 18, 2016

(87) PCT Pub. No.: WO2015/126045
PCT Pub. Date: Aug. 27, 2015

(65) Prior Publication Data
US 2017/0049393 A1    Feb. 23, 2017

(30) Foreign Application Priority Data

Feb. 18, 2014   (KR) ................. 10-2014-0018467

(51) Int. Cl.
*A61B 5/157*   (2006.01)
*A61B 5/155*   (2006.01)
(Continued)

(52) U.S. Cl.
CPC .......... *A61B 5/682* (2013.01); *A61B 5/14503* (2013.01); *A61B 5/14528* (2013.01); *A61B 5/155* (2013.01); *A61B 5/157* (2013.01); *A61B 5/150015* (2013.01); *A61B 5/150022* (2013.01); *A61B 5/150045* (2013.01);
(Continued)

(58) Field of Classification Search
CPC . A61B 5/682; A61B 5/14503; A61B 5/14528; A61B 5/150015; A61B 5/150022; A61B 5/150045; A61B 5/150755; A61B 5/150839; A61B 5/150877; A61B 5/155; A61B 5/157; A61B 5/686; A61B 5/14532;
(Continued)

(56) References Cited

U.S. PATENT DOCUMENTS 6,400,972 B1   6/2002   Fine
6,599,406 B1   7/2003   Kawanaka et al.
(Continued)

FOREIGN PATENT DOCUMENTS

KR   10-0675463 B1   1/2007
KR   10-0731716      6/2007
(Continued)

OTHER PUBLICATIONS

International Search Report and Written Opinion for corresponding Patent Application No. PCT/KR2014/012066 dated Jan. 9, 2015.

*Primary Examiner* — Navin Natnithithadha
(74) *Attorney, Agent, or Firm* — Renner, Otto, Boisselle & Sklar, LLP

(57) ABSTRACT

Provided is a non-invasive blood measuring device comprising: a fixture which in part or in whole is buried in bone tissue of a patient; an abutment provided in a space inside the fixture; a sensing unit including biosensors for measuring a substance in the blood; a filter through which the substance in the blood to be measured is passed through; and an outcall unit.

8 Claims, 7 Drawing Sheets

(51) Int. Cl.
*A61B 5/145* (2006.01)
*A61B 5/00* (2006.01)
*A61B 5/15* (2006.01)
*A61C 8/00* (2006.01)

(52) U.S. Cl.
CPC .. *A61B 5/150755* (2013.01); *A61B 5/150839* (2013.01); *A61B 5/150877* (2013.01); *A61B 5/686* (2013.01); *A61C 8/006* (2013.01); *A61C 8/0037* (2013.01); *A61C 8/0068* (2013.01); *A61C 8/0069* (2013.01); *A61C 8/0074* (2013.01); *A61B 5/14532* (2013.01); *A61B 5/14535* (2013.01)

(58) Field of Classification Search
CPC ... A61B 5/14535; A61C 8/006; A61C 8/0068; A61C 8/0069; A61C 8/0074
USPC .......................................... 600/309, 345–366
See application file for complete search history.

(56) References Cited

U.S. PATENT DOCUMENTS

| | | | |
|---|---|---|---|
| 7,035,684 B2 * | 4/2006 | Lee | A61B 5/0031 600/513 |
| 7,955,492 B2 | 6/2011 | Fujiwara et al. | |
| 2004/0167416 A1 * | 8/2004 | Lee | A61B 5/0031 600/513 |
| 2009/0268194 A1 | 10/2009 | Tomita | |
| 2010/0145317 A1 * | 6/2010 | Laster | A61B 5/0031 604/891.1 |
| 2013/0144144 A1 * | 6/2013 | Laster | A61M 37/00 600/365 |

FOREIGN PATENT DOCUMENTS

| KR | 10-2009-0112560 A | 10/2009 |
|---|---|---|
| KR | 10-1108381 B1 | 1/2012 |

* cited by examiner

[Figure 1]
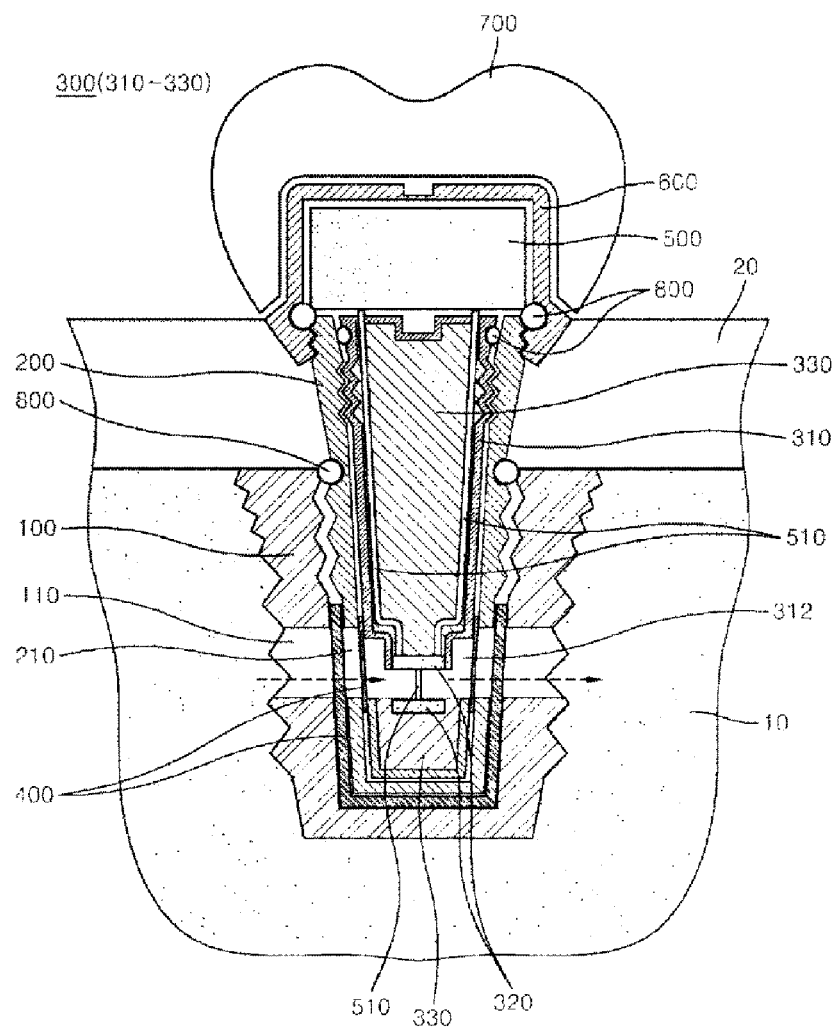

【Figure 2】
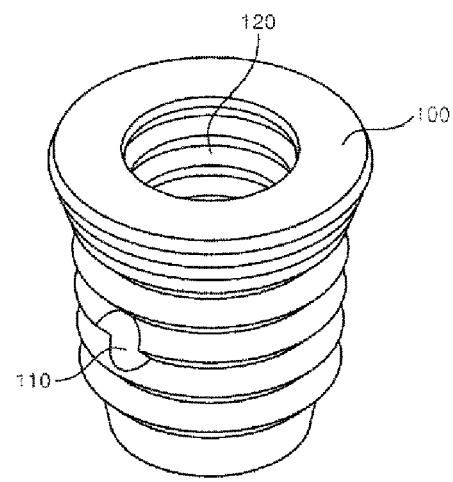
【Figure 3】
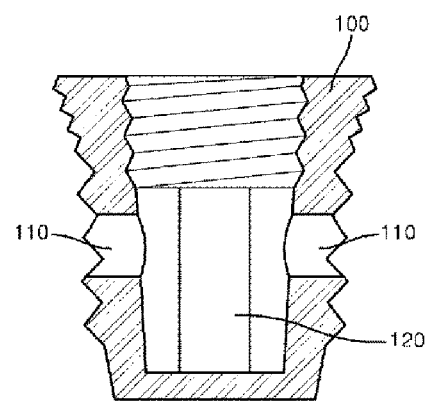

[Figure 4]
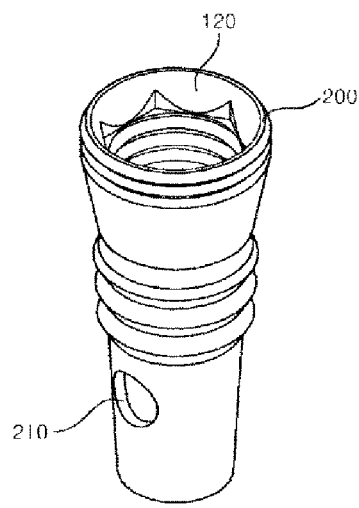
[Figure 5]
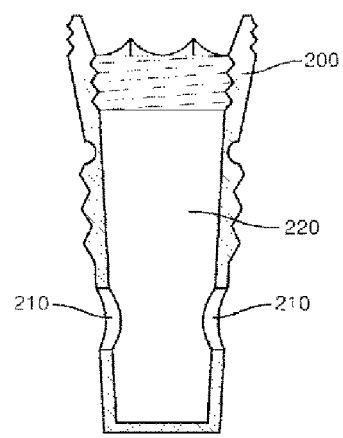

[Figure 6]
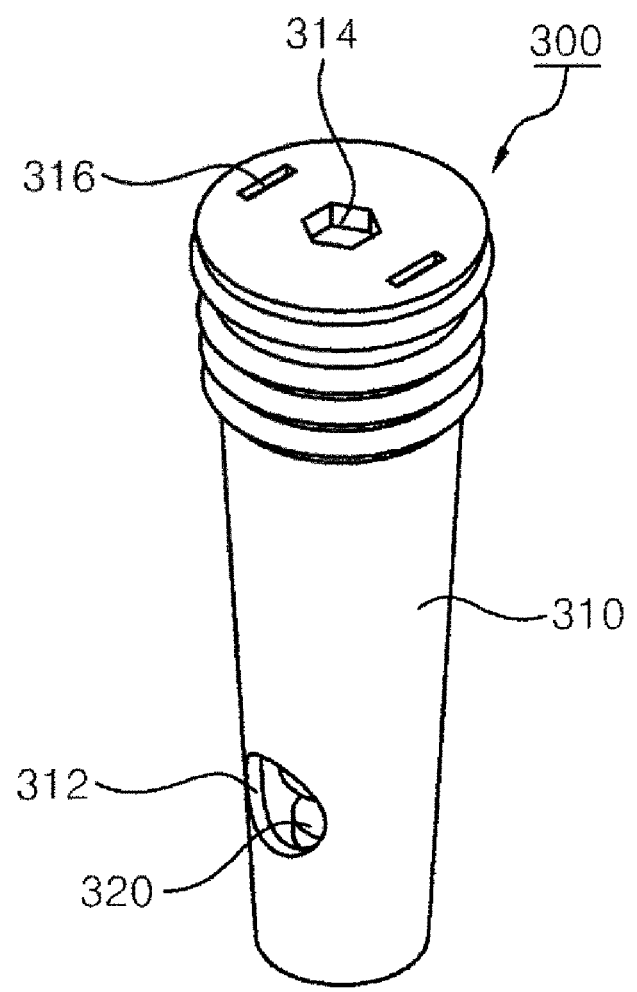

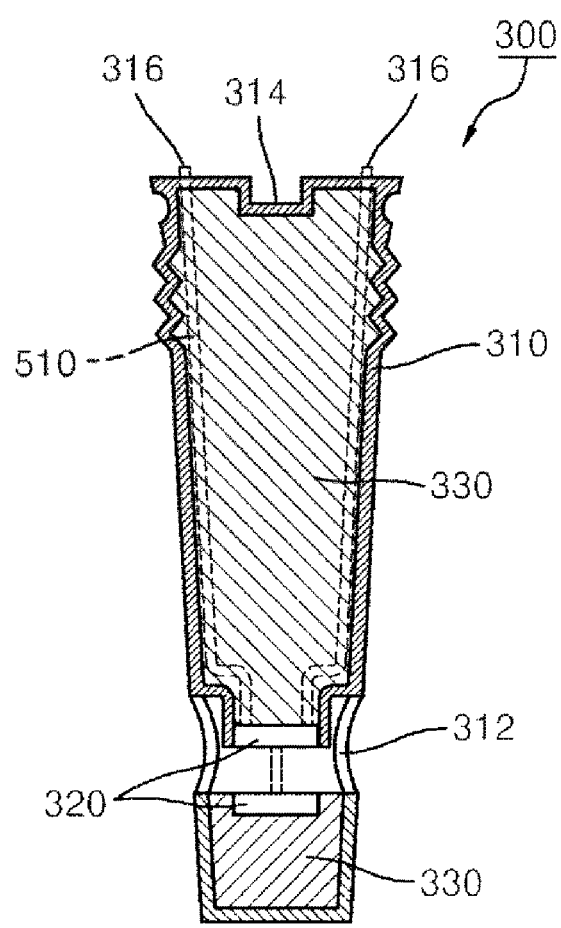
[Figure 7]

【Figure 8】
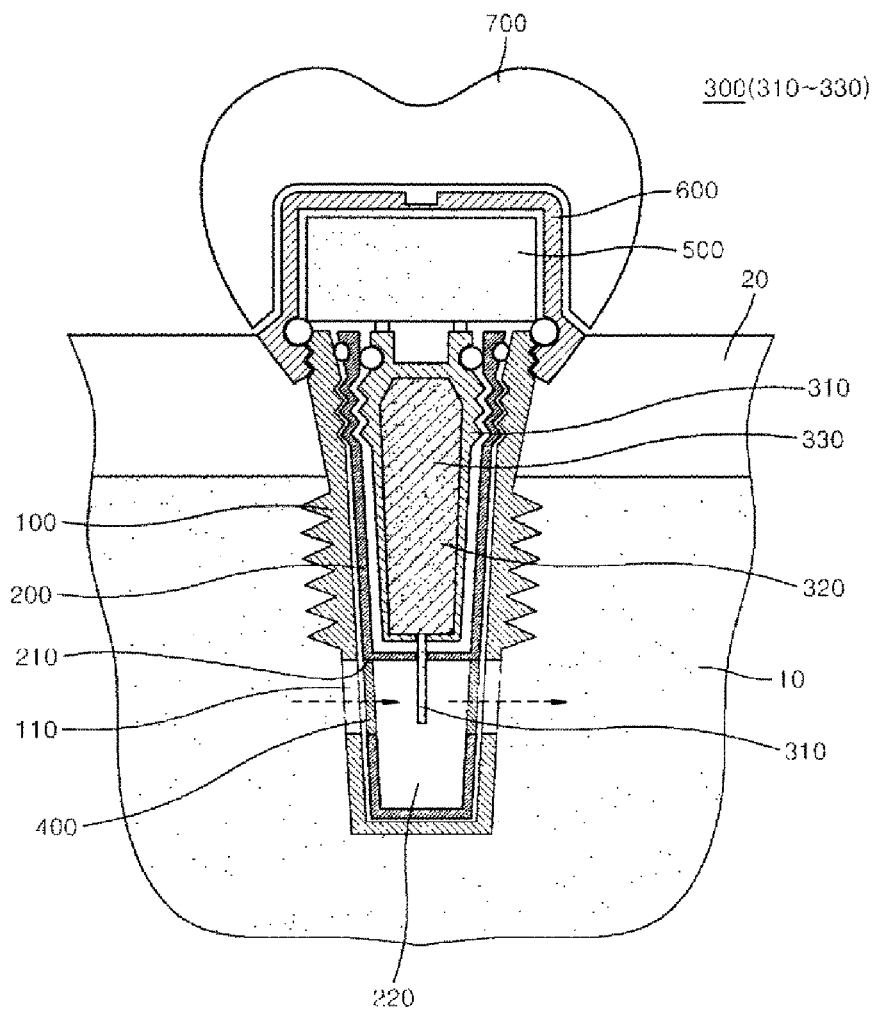

【Figure 9】
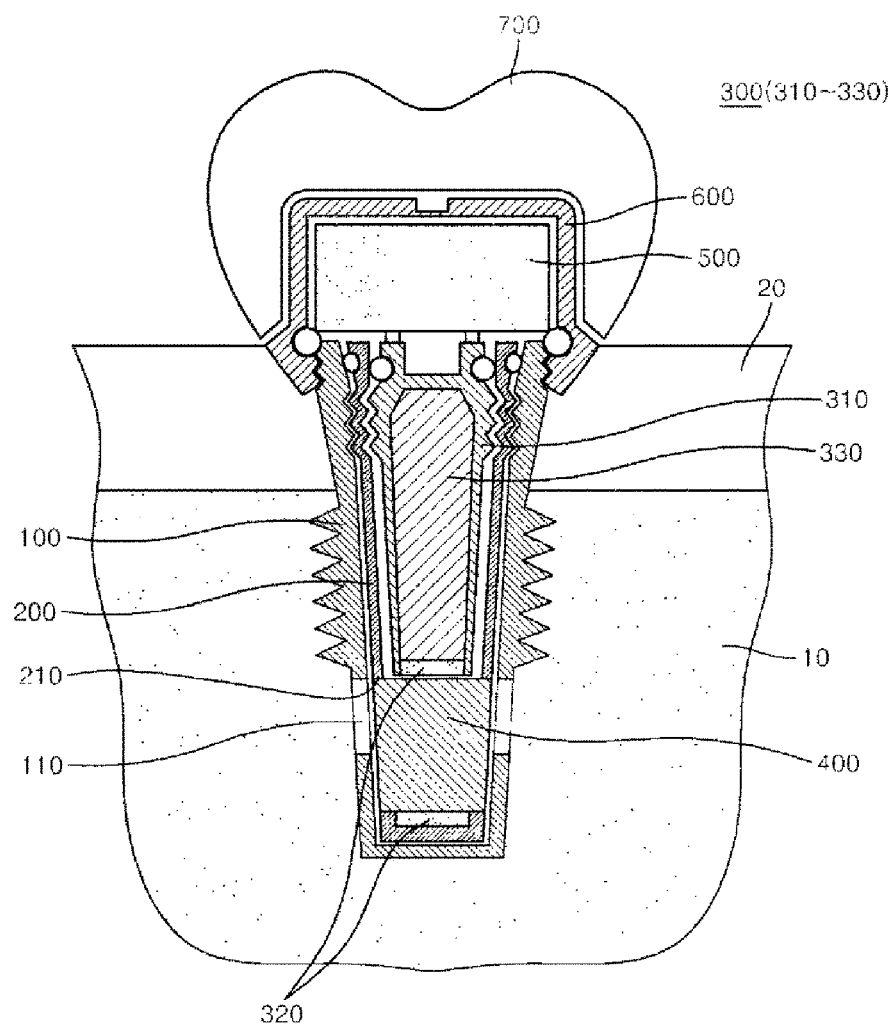

NON-INVASIVE BLOOD MEASURING DEVICE

TECHNICAL FIELD

The present disclosure relates to a non-invasive blood measuring device.

BACKGROUND ART

Recently, as living environments have significantly improved and living conditions have become better, individuals are increasingly interested in personal health. As a result, a significant amount of research into home medical devices allowing users to easily check their personal physical condition has been conducted and new products have been developed one after another.

In case of a healthy individual, generally, body fluid present within a living body is organically circulated and adjusted to maintain an amount of a body fluid in a predetermined range. Here, body fluid includes constituents such as blood, urine, interstitial fluid, perspiration, and saliva, and in particular, concentrations of constituents of blood, urine (carbohydrates or protein), and the like, in body fluid, are critical indicators indicating a person's physical condition. As for blood, it is important to measure a concentration of constituents such as glucose, hemoglobin, bilirubin, cholesterol, albumin, creatinine, protein, urea, and the like, present in blood.

However, when a living body is afflicted with a disease, a composition or an amount of body fluid constituents may be changed, causing a risky health situation. For example, a concentration of blood glucose is about 80 mg/dl before a meal and about 120 mg/dl after a meal in a healthy individual, and in order to maintain the concentration of blood glucose, the pancreas secretes an appropriate amount of insulin before or after a meal, the secreted insulin being absorbed by the liver and bowels (intestines) and skeletal muscle cells in a living body. Here, if insulin in an amount required for maintaining normal blood glucose is not produced by the pancreas due to a disease or some other reason, an excessive amount of glucose may be present in blood to potentially cause a cardiac disorder or a liver disease, arteriosclerosis, high blood pressure, cataracts, a retinal hemorrhage, neural damage, hearing loss, amblyopia, and the like, and in a worst case scenario, a corresponding patient may die. Thus, it is important to periodically measure a change in constituents of a body fluid of a living body before such an extreme result occurs.

A method for measuring a concentration of blood constituents includes an invasive method of directly collecting a portion of a target material and performing measurement thereon and a non-invasive method of performing measurement without collecting a target material. Due to various problems of the invasive method, technologies to easily diagnose blood liquid constituents in a non-invasive manner have continued to be developed.

For example, in order to measure blood glucose in the existing invasive manner, blood is collected and reacted with a diagnostic reagent, and a clinical analysis device is used or discoloration of a test strip which has reacted with the reagent is quantified. In a case in which blood collection is performed several times every day, a patient may experience a significant amount of pain, may have a high probability of being infected with a disease, and may find it difficult to continuously monitor blood constituents so the patient may have difficulty in properly coping with an emergency as it occurs. In addition, in the case of the strip or the reagent, a large amount of consumables must be used, imposing a financial burden on a user, and such consumables are environmental contamination materials required to be handled in compliance with proper regulations. Also, in the case of a cancer patient, a cancer cell may spread to other organs through blood so whether a cancer cell has spread may be determined through blood constituent test. Here, however, blood should be collected from the cancer patient each time when necessary for a test.

Thus, in order to adjust blood sugar of diabetic patients, determine whether a cancer cell of a cancer patient has spread, or for a physical checkup of a healthy individual, a technology for continuously measuring constituents required for a test in a non-contaminated environment within a living body, without a strip or a consumable or without blood collection, to accurately diagnose a patient condition is required. In order to achieve the object, non-invasive blood measuring devices have been actively researched. For example, Korean Patent Registration No. 10-0731716 discloses contents regarding non-invasive optical measurement of blood constituents (or blood components). However, conventional non-invasive blood measuring devices are inconvenient to use and relatively expensive while a non-invasive blood measuring device that may be easily purchased and used by patients is relatively rare.

DISCLOSURE

Technical Problem

An aspect of the present disclosure is to obtain blood from a patient without a separate invasive process without causing pain to the patient and to periodically measure and transmit a blood condition of a patient to allow an emergency situation to be coped with effectively.

Another aspect of the present disclosure is to facilitate usage and reduce costs.

Exemplary embodiments of the present disclosure may also be used to achieve any other technical solution not specifically mentioned in addition to the foregoing technical solution.

Technical Solution

According to an aspect of the present invention, a non-invasive blood measuring device may include: a fixture including an internal space fixture including an open region and a fixture through hole penetrating through the internal space fixture, and partially or entirely embedded in bone tissue of a patient; an abutment positioned in the internal space fixture; a sensing unit including a biosensor measuring a constituent of blood introduced through the fixture through hole and provided within the abutment; a filter allowing a constituent of blood as a measurement target to pass therethrough and positioned in the fixture through hole; and a transmission unit transmitting a signal generated by the biosensor outwardly.

The abutment may include an internal abutment space including an open region and an abutment through hole penetrating through the internal abutment space, a housing inserted into the internal abutment space or integrated with the abutment may be provided, the housing may include a housing through hole positioned in a location corresponding to the abutment through hole, and one or more biosensors may be installed within the housing.

The filter may include a first filter positioned between an inner surface of the fixture and an outer surface of the abutment and a second filter positioned between an inner surface of the abutment and an outer surface of the housing, or both of the first filter and the second filter.

The abutment may be led to an upper side of a point at which the fixture through hole is positioned in the internal space fixture, and the biosensor may extend in a direction toward the fixture through hole from a lower side of the abutment.

The abutment may be led to an upper side of a point at which the fixture through hole is positioned in the internal space fixture, and the filter may have a block shape filling a portion of the internal space fixture.

The internal space fixture may have an overall polygonal recess shape or a portion of the internal space fixture may have a polygonal recess shape.

The entirety of the fixture may be embedded in bone tissue of a patient and an upper surface thereof may be exposed outwardly of the bone tissue, and a lower portion of the abutment may be inserted into the internal space fixture and an upper end thereof may be exposed outwardly of soft tissue of the patient.

A lower portion of the fixture may be embedded in bone tissue of the patient and an upper surface thereof may be exposed outwardly of the soft tissue of the patient, and the abutment may be entirely inserted into the internal space fixture.

Advantageous Effects

According to exemplary embodiments of the present disclosure, blood constituents of the patient may be periodically analyzed within a living body and transmitted, various diseases may be diagnosed and easily managed, an emergency situation as occurs may be handled at an early stage, and a patient's physical conditions may be more easily and accurately managed, without using an invasive method causing physical and mental pain as well as inconvenience, while damaging a patient's body.

DESCRIPTION OF DRAWINGS

FIG. 1 is a cross-sectional view of a non-invasive blood measuring device according to an exemplary embodiment.

FIGS. 2 and 3 are a perspective view and a cross-sectional view of a fixture.

FIGS. 4 and 5 are a perspective view and a cross-sectional view of an abutment.

FIGS. 6 and 7 are a perspective view and a cross-sectional view of a sensing unit.

FIG. 8 is a cross-sectional view of a non-invasive blood measuring device according to an exemplary embodiment.

FIG. 9 is a cross-sectional view of a non-invasive blood measuring device according to an exemplary embodiment.

BEST MODE FOR INVENTION

Hereinafter, exemplary embodiments will be described in detail with reference to the accompanying tables and drawings such that they can be easily practiced by those skilled in the art to which the present invention pertains. As those skilled in the art would realize, the described exemplary embodiments may be modified in various different ways, all without departing from the spirit or scope of the present invention. In the accompanying drawings, a portion irrelevant to description of the present invention will be omitted for clarity, and like reference numerals refer to like elements throughout. Also, detailed descriptions of a known art will be omitted.

Throughout the specification, unless explicitly described to the contrary, the word "comprise" and variations such as "comprises" or "comprising" will be understood to imply the inclusion of stated elements but not the exclusion of any other elements.

Hereinafter, a non-invasive blood measuring device will be described in detail with reference to the accompanying drawings.

FIG. 1 is a cross-sectional view of a non-invasive blood measuring device according to an exemplary embodiment, FIGS. 2 and 3 are a perspective view and a cross-sectional view of a fixture, FIGS. 4 and 5 are a perspective view and a cross-sectional view of an abutment, and FIGS. 6 and 7 are a perspective view and a cross-sectional view of a sensing unit.

A non-invasive blood measuring device according to an exemplary embodiment is able to collect blood and inspect blood even though a needle is not inserted into the skin of a patient, and is embedded within an implant to periodically inspect blood of the patient without inflicting additional pain on the patient.

The non-invasive blood measuring device includes a fixture 100 implanted in bone tissue 10 of a patient, an abutment 200 threaded (or screw-coupled) to an interior of the fixture 100, a sensing unit 300, a filter 400, a transmission unit 500 for transmitting a measurement signal, and a cover 600 formed to have a cap shape covering an upper side of an internal space 220 of the abutment 200 and coupled to the fixture 100 or the abutment 200 on a lower side thereof. The cover 600 may be omitted, and a tooth prosthetic appliance 700 may be mounted on the cover 600.

The fixture 100 and the abutment 200 may have a basic structure similar to that applied to a general implant. A through hole is formed in each of an interior of the fixture 100 and the abutment 200 to allow blood flowing in a vicinity of the bone to pass through the interior of the fixture 100 and the abutment 200. The fixture 100 includes a internal space fixture 120 including an open region and a fixture through hole 110 penetrating through the internal space fixture 120. The abutment 200 includes an internal abutment space 220 including an open region and an abutment through hole 210 penetrating through the internal abutment space 220.

The sensing unit 300 includes a housing 310, a biosensor 320, and a signal processing component 330. The housing 310 may be installed in the internal space 220 as a separation type housing or may be integrated with the abutment 200. The biosensor 320 may be coupled to the housing 310 and measure blood and tissue fluid constituents (hereinafter, referred to as "blood") introduced through the fixture through hole 110 and the abutment through hole 210. The signal processing component 330 may be installed within the housing 310 and processes a signal generated by the biosensor 320. The signal processing component 330 may also be installed within the cover 600 or the transmission unit 500, or may be positioned outside of the body. For example, the signal processing component 330 may merely transmit a signal sensed by the biosensor 320 to the outside through the transmission unit 500 and any other signal processing may be performed by an external system. In a case in which the abutment 200 and the housing 310 are integrated, the abutment 200 may substitute for the role of the housing 310 and the biosensor 320 and the signal processing component 330 may be directly installed within the abutment 200. In this manner, when the abutment 200 substitutes for the role of the housing 310, the number of components to be provided within the internal space of the fixture 100 is reduced, more extensively securing a space for installation of the signal processing component 330. Any sensor such as an optical sensor measuring a concentration of blood glucose using light, an electrical sensor using an electrical signal, a composite sensor using two or more methods complexly may be applied as the biosensor 320 as long as it can measure blood constituents. Sensors having various structures to measure blood constituents have been proposed, so a detailed description thereof will be omitted.

The transmission unit 500 is connected to the biosensor 320 through an electric wire 510 extending vertically through an electric wire outlet 316 of the housing 310, and accordingly, a current flows between the transmission unit 500 and the biosensor 320 and a signal may be transmitted therebetween. Also, the transmission unit 500 may be mounted above the housing 310, and in this case, the transmission unit 500 may be easily replaced in the event of discharging. The transmission unit 500 and the biosensor 320 may transmit signals to each other through wireless communications, as well as through wired communications. Also, the transmission unit 500 may include a power source.

An O-ring 800 may be provided between the fixture 100 and the abutment 200, between the abutment 200 and the housing 310, and between the abutment 200 and the cover 600 in order to maintain airtightness.

When the blood measuring device according to an exemplary embodiment of the present disclosure is used, blood flowing around a bone may be introduced through the fixture through hole 110 and subsequently introduced to the internal abutment space 220 through the abutment through hole 210, even without a separate blood collecting device, and thus, the biosensor 320 may measure various constituents of the blood introduced to the internal abutment space 220. Blood passing through the biosensor 320 sequentially passes through the abutment through hole 210 and the fixture through hole 110 on the opposite side and is discharged to a vicinity of the bone, and accordingly, the biosensor 320 may accurately measure newly supplied blood always, and thus, a blood state of a patient may be measured and transmitted in real time. Therefore, a user of the blood measuring device according to an exemplary embodiment may be able to promptly cope with an emergency situation of a patient.

The blood measuring device according to an exemplary embodiment may also perform a dental implant function. Thus, in a case in which a patient who intends to receive a dental implant wants to measure a portion of blood constituents, in addition to a basic function of the implant, the blood measuring device according to an exemplary embodiment, instead of an existing implant, may be implanted and the tooth prosthetic appliance 700 may be mounted thereon, eliminating the necessity of installation of a separate additional device.

When a lifespan of the biosensor 320 or the transmission unit 500 comes to an end and is required to be replaced, the transmission unit 500 and the sensing unit 300 may be replaced by simply removing only the tooth prosthetic appliance 700 and the cover 600, while the fixture 100 and the abutment 200 are maintained in a state of being coupled to the bone tissue 10, and thus, maintenance and repair are very easy.

In a case in which the fixture through hole 110 has an open structure, cells and constituents (hereinafter, referred to as an "osteoblast") causing osteanagenesis may increase, and the fixture through hole 110 and the abutment through hole 210 may be filled with bone with the lapse of a predetermined period of time to make it impossible to transmit blood to the biosensor 320.

Thus, the filter 400 reducing passage of an osteoblast and allowing components in blood to be tested to pass therethrough may be attached to the fixture through hole 110. In general, cells or constituents participating in bone formation like an osteoblast may be greater than constituents of a material to be sensed, that is, blood and interstitial fluid, in size. Thus, a possibility that the area in which the biosensor 320 is placed is filled with bone to degrade sensitivity of the biosensor 320 may be reduced by the filter 400 and a large amount of sensing targets such as glucose molecules in blood may be allowed to pass through the filter 400, increasing accuracy of measurement of the biosensor 320. In addition, the filter 400 may be positioned in the abutment through hole 210. Also, several filters 400 may be installed in a passage where blood passes, such as the fixture through hole 110, the abutment through hole 210, and the like.

In a case in which the filter 400 is provided to have a size not allowing cell constituents (for example, white blood cells, red blood cells, and the like) in blood that may interfere with a sensing operation, only sensing targets may be introduced to the biosensor 320, and thus, the biosensor 320 may sense more pure samples. A size of the filter 400 may be variously modified according to types of targets to be sensed by the biosensor 320 or various measurement conditions.

Also, a type, a structure, a function, and the like, of the filter 400 have been variously presented to date, so descriptions thereof will be omitted.

Pressure of about 20 mmHg corresponding to about 17% of blood pressure of the whole body enables blood to flow within bone, and such pressure acts as driving force to filter required constituents when blood passes through the filter 400, lowering a possibility that blood flowing within the bone to be absorbed to the filter 400 or pool therein.

For example, sizes of constituents within blood and sizes of pores of microfilters may be as follows.

<Sizes of Constituents within Blood>
Osteocyte: About 5-20 micrometers
Osteoblast: About 20-30 micrometers
Red blood cell (RBC): About 8.5 micrometers in diameter, and about 2.4 micrometers in thickness
White blood cell (WBC): About 12-15 micrometers
Platelet: About 2-4 micrometers
Glucose molecules: About 1 micrometer
<Types of Filter and Sizes of Pore>
Micro filtration (MF): About 0.1-10 micrometers
Ultra filtration (UF): About 0.01 micrometers
Nano filtration (NF): About 0.001 micrometers
Reverse Osmosis (RO): About 0.001 micrometers Even rough comparison shows that there is significant difference between the blood constituents and the sizes of pores of the filters, and thus, the filters may smoothly perform a filtering function in a state of not being clogged.

In order to install a larger amount of signal processing components 330 within the housing 310, the housing 310 is required to fill most of the internal abutment space 220. In this manner, in a case in which the housing 310 fills most of the internal abutment space 220, a housing through hole 312 may be formed in a portion of a side wall of the housing 310 corresponding to the abutment though hole 210 so that blood introduced through the abutment through hole 210 may be transmitted to the biosensor 320, and the biosensor 320 may be installed on an inner surface of the housing through hole 312. Here, the biosensor 320 may be provided on each of a bottom surface and a ceiling surface of the housing through hole 312, or may be provided on a side wall of the housing through hole 312. Also, the installation number of biosensors 320 may be variously modified. For example, one or a plurality of biosensors 320 may be installed.

In order to more restrict constituents transmitted to the biosensor 320, that is, in order to more reliably filter blood transmitted to the biosensor 320, the filter 400 may also be installed in the abutment through hole 210, as well as in the fixture through hole 110. Here, in order to maintain the filter 400 in a stably fixed state, the filter 400 covering the fixture through hole 110 may be compressed between an inner surface of the fixture 100 and an outer surface of the abutment 200, and the filter 400 covering the abutment through hole 210 may be compressed between an inner surface of the abutment 200 and an outer surface of the housing 310.

While the fixture 100 is fixedly coupled to the bone tissue 10 in a threaded manner (or in a screw-coupled manner), the abutment 200, the housing 310, and the cover 600 may be coupled to the bone tissue 10 in a detachable manner, to facilitate maintenance of the blood measuring device. For example, the abutment 200, the housing 310, and the cover 600 may be coupled in a threaded manner. In order to rotate the fixture 100, the abutment 200, the housing 310, and the cover 600 through a tool such as a wrench may be used, that is, in order to allow ends of a tool such as a wrench to be inserted in a fitting manner, the entirety or a portion of the internal space fixture 120 and the internal abutment space 220 may have a polygonal recess shape, and a polygonal recess may be formed in an upper surface of the housing 310 and an upper surface of the cover 600. The structure in which the abutment 200 is coupled to the fixture 100 in a threaded manner is widely known in a general implant, and thus, a detailed description thereof will be omitted. Also, if the fixture 100 and the abutment 200 are configured to have a threaded structure, the fixture through hole 110 and the abutment through hole 210 may not be aligned but deviate according to rotation angles of the abutment 200, and thus, a guide marker (not shown) may be provided in each of an outer surface of the fixture 100 and an outer surface of the abutment 200 in order to uniformly set a thread angle therebetween.

FIG. 8 is a cross-sectional view of a non-invasive blood measuring device according to an exemplary embodiment of the present disclosure.

As illustrated in FIG. 1, the fixture 100 may be coupled to the bone tissue 10 such that the entirety thereof is embedded in the bone tissue 10 of a patient and only an upper surface thereof is exposed, and as illustrated in FIG. 8, only a lower portion of the fixture 100 may be embedded in the bone tissue 10 and upper portion thereof may protrude upwardly from the bone tissue 10 and coupled such that an upper surface thereof is exposed to an outer side of soft tissue 200 of the patient. In a case in which the fixture 100 is entirely embedded in the bone tissue 10, only a portion of the abutment 200 may be inserted into the internal space fixture 120. In a case in which the fixture 100 is manufactured such that the top thereof is exposed to the outside of the soft tissue 20, the entirety of the abutment 200 may be inserted into the internal space fixture 120.

In a case in which the upper surface of the fixture 100 is exposed to the outside of the soft tissue 20, since the cover 600 is couple to the top of the fixture 100, an outer diameter of the fixture 100 may be slightly reduced. In a case in which the outer diameter of the fixture 100 is reduced, interference with another implant may be avoided, and a possibility of damage to a bone that may be caused when the fixture 100 is implanted may be reduced. Also, since a diameter of an installation hole formed in the bone tissue 10 to install the fixture 100 is reduced, the bone tissue 10 may have strength maintained to be equal to or greater than a reference value.

The signal processing component 330 installed within the housing 310 is relatively small, the housing 310 may be short in length so that the housing 310 may be led in to a portion of the internal abutment space 220 where the abutment through hole 210 is positioned. In a case in which the housing 3100 is positioned above a spot of the internal abutment space 220 where the abutment through hole 210 is positioned, in order to allow the biosensor 320 to come into contact with blood passing through the abutment through hole 210, the biosensor 320 may be configured such that an upper portion thereof is connected to the signal processing component 330 and a lower portion thereof extends downwardly to an interior of the abutment through hole 210. For example, the biosensor 320 may have a bar shape extending in a vertical direction.

In a case in which the housing 310 is installed only in an upper portion of a point of the internal abutment space 220 where the abutment through hole 210 is positioned, a space below the housing in the internal abutment space 220 may be entirely utilized as a sensing space 220 for a sensing operation, whereby blood constituents may be measured in more various manners.

As illustrated in FIG. 8, the structure in which the housing 310 is installed above a point at which the abutment through hole 210 is positioned in the internal abutment space 220 and the biosensor 320 extends downwardly may also be applied to the case in which the fixture 100 is completely embedded in the bone tissue 10 as illustrated in FIG. 1.

FIG. 9 is a cross-sectional view of a non-invasive blood measuring device according to an embodiment of the present disclosure.

The filter 400 may be manufactured to have a sheet shape as illustrated in FIGS. 1 to 8, or may be manufactured to have a block shape filling the entirety or a portion of the interior of the abutment 200. Here, the biosensor 320 is installed in a lower portion of the abutment 200 and may face an upper surface or a lower surface of the filter 400. In addition, the through hole 210 of the abutment 200 may be omitted, and in this case, a lower surface of the abutment 200 may be positioned in the vicinity of the through hole 110 of the fixture 100.

In a case in which the filter 400 is manufactured to have a block shape, a speed of blood flow may be slightly lowered, but blood may be more effectively filtered and more pure blood sample may be provided to the biosensor 320. The block-shaped filter 400 may also be applied to even in a case in which the fixture 100 is completely embedded in the bone tissue 10 as illustrated in FIG. 1.

While exemplary embodiments have been shown and described above, it will be apparent to those skilled in the art that modifications and variations could be made without departing from the scope of the present disclosure as defined by the appended claims.

The invention claimed is:
1. A non-invasive blood measuring device comprising:
 a fixture including an internal space fixture including an open region and a fixture through hole penetrating through the internal space fixture, and partially or entirely embedded in bone tissue of a patient;
 an abutment positioned in the internal space fixture;

a sensing unit including a biosensor measuring a constituent of blood introduced through the fixture through hole and provided within the abutment;

a filter allowing a constituent of blood as a measurement target to pass therethrough and positioned in the fixture through hole; and a transmission unit transmitting a signal generated by the biosensor outwardly.

2. The non-invasive blood measuring device of claim 1, wherein the abutment includes an internal abutment space including an open region and an abutment through hole penetrating through the internal abutment space, a housing inserted into the internal abutment space or integrated with the abutment is further provided, the housing includes a housing through hole positioned in a location corresponding to the abutment through hole, and one or more biosensors are installed within the housing.

3. The non-invasive blood measuring device of claim 2, wherein the filter includes a first filter positioned between an inner surface of the fixture and an outer surface of the abutment and a second filter positioned between an inner surface of the abutment and an outer surface of the housing, or both of the first filter and the second filter.

4. The non-invasive blood measuring device of claim 1, wherein the abutment is led to an upper side of a point at which the fixture through hole is positioned in the internal space fixture, and the biosensor extends in a direction toward the fixture through hole from a lower side of the abutment.

5. The non-invasive blood measuring device of claim 1, wherein the abutment is led to an upper side of a point at which the fixture through hole is positioned in the internal space fixture, and the filter has a block shape filling a portion of the internal space fixture.

6. The non-invasive blood measuring device of claim 1, wherein the internal space fixture has an overall polygonal recess shape or a portion of the internal space fixture has a polygonal recess shape.

7. The non-invasive blood measuring device of claim 1, wherein the entirety of the fixture is embedded in bone tissue of a patient and an upper surface thereof is exposed outwardly of the bone tissue, and a lower portion of the abutment is inserted into the internal space fixture and an upper end thereof is exposed outwardly of soft tissue of the patient.

8. The non-invasive blood measuring device of claim 1, wherein a lower portion of the fixture is embedded in bone tissue of the patient and an upper surface thereof is exposed outwardly of the soft tissue of the patient, and the abutment is entirely inserted into the internal space fixture.

* * * * *